US00PP35755P2

(12) United States Plant Patent
Van Swieten

(10) Patent No.: US PP35,755 P2
(45) Date of Patent: Apr. 16, 2024

(54) ***PHALAENOPSIS* ORCHID PLANT NAMED 'PHA191366'**

(50) Latin Name: ***Phalaenopsis* hybrid**
Varietal Denomination: PHA191366

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,130

(22) Filed: Apr. 18, 2023

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
*Assistant Examiner* — Zachariah Allan Kay
(74) *Attorney, Agent, or Firm* — Jondle & Associates, P.C.

(57) ABSTRACT

A new and distinct variety of *Phalaenopsis* plant named 'PHA191366', particularly characterized by having large white flowers with yellow-green and white lips, flowers that are concave in lateral view, strong lip curvature of lateral lobe, and is propagated by meristem tissue culture, is disclosed.

3 Drawing Sheets

Genus and species: *Phalaenopsis* hybrid.
Variety denomination: 'PHA191366'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA191366'.

The new *Phalaenopsis* plant is a product of a planned breeding program conducted by the inventor in Bleiswijk, the Netherlands. The objective of this breeding program was to create a new *Phalaenopsis* plant with numerous attractive white, large flowers with yellow-green and white lips, suitable for potted plant production.

The new *Phalaenopsis* plant 'PHA191366' is a result of cross-pollination made by the inventor in December 2014 in Bleiswijk, the Netherlands, of the proprietary female, or seed parent, *Phalaenopsis* hybrid '00001-4911' (unpatented) with the proprietary male, or pollen parent, *Phalaenopsis* hybrid 'PHALFYTBE' (U.S. Plant Pat. No. 30,484).

The new *Phalaenopsis* was selected by the inventor as a single plant within the progeny of the stated cross-pollination in a controlled greenhouse in Bleiswijk, the Netherlands, in July 2018. Asexual reproduction of the new *Phalaenopsis* plant by meristem tissue culture since 2019 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 24, 2022 (Application no. 2022/1983), by Applicant who obtained the subject matter disclosed directly from the inventor. 'PHA191366' has not been made publicly available or sold anywhere in the world prior to the effective filing date of this application with the exception of sales or disclosures made one year or less before the effective filing date of this claimed invention by Applicant who obtained 'PHA191366' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA191366' as a new and distinct variety of *Phalaenopsis* plant:

1) Large, white flowers with yellow-green and white lips;
2) Flower shape in lateral view is concave; and
3) Strong lip curvature of lateral lobe.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2023. Colors in the photographs may differ from the color values cited in the detailed botanical description, which accurately describe the actual colors of the new variety.

DESCRIPTION OF THE NEW VARIETY

Figure 1:
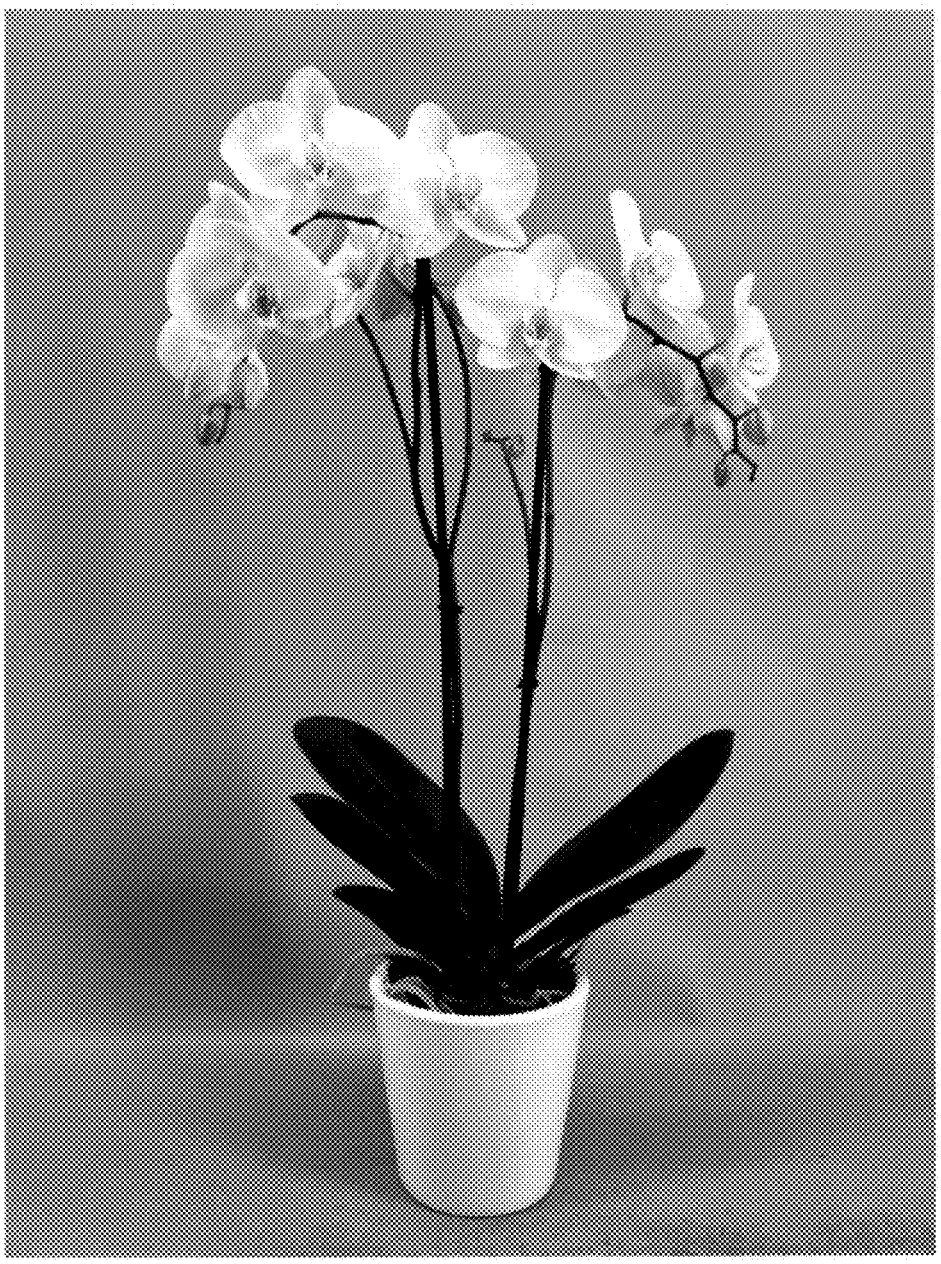
FIG. 1 shows the overall plant habit, including blooms, buds, and foliage of 'PHA191366'.
Figure 2:
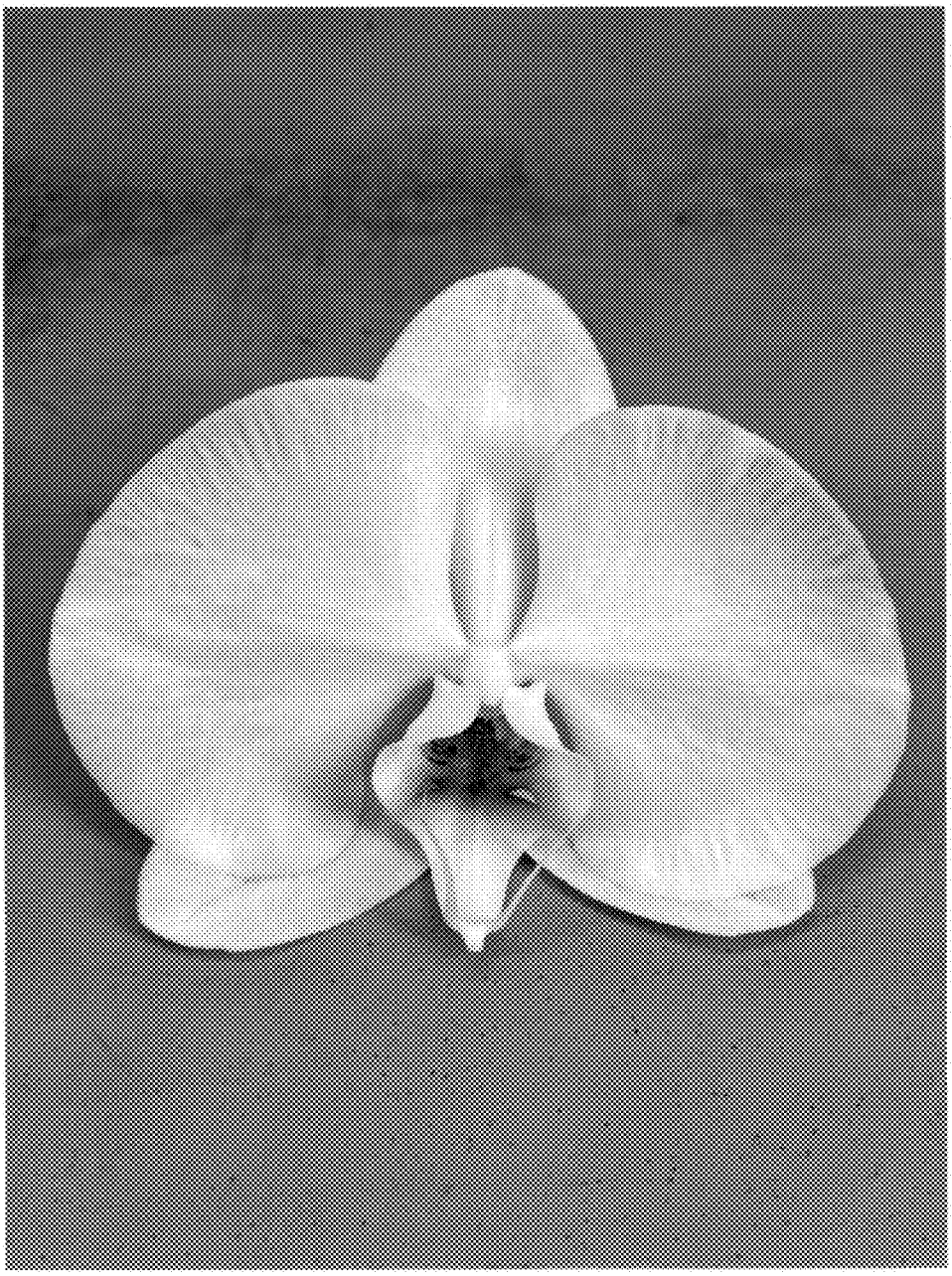
FIG. 2 shows a close-up of a flower of 'PHA191366'.
Figure 3:
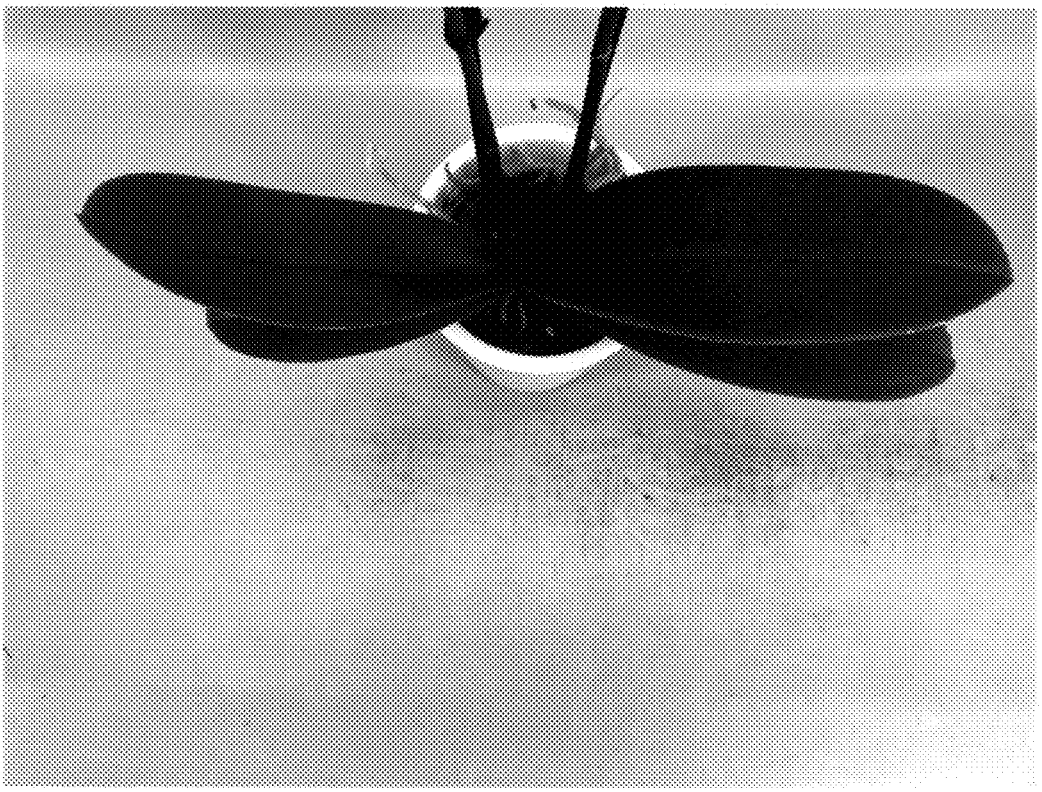
FIG. 3 shows an overhead, close-up view of the leaves of 'PHA191366'.

The following detailed description sets forth the distinctive characteristics of 'PHA191366'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA191366'.

Parentage:

*Female parent*.—*Phalaenopsis* cultivar '000014911' (unpatented).

*Male parent*.—*Phalaenopsis* cultivar 'PHALFYTBE' (U.S. Plant Pat. No. 30,484).

Propagation:

*Type*.—Meristem tissue culture.

Roots:

*Root description*.—Greyed-green (a color in between RHS 190B and RHS 190C) colored roots with branching lateral roots having yellow-green (RHS 144C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 61.0 cm to 71.0 cm.

*Width* (*measured from leaf tips*).—About 39.0 cm to 41.0 cm.

*Vigor*.—Strong.

Leaves:

*Mature leaves*.—Quantity per plant: 8 to 10 leaves are produced before flowering. Length (fully expanded): 21.0 cm to 23.0 cm. Width: 7.5 cm to 8.5 cm. Position of the broadest part of the leaf: At the middle. Shape: Oblong. Base shape: Moderately elongated. Apex: Obtuse asymmetric. Leaf blade angle with the petiole (measured from the horizontal position): Between 30 degrees and 50 degrees. Leaf margin: Entire. Color: Upper surface: RHS 147A. Lower surface: RHS 146A. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146A.

Peduncle:

*Quantity per plant*.—2.

*Number of flowers per peduncle*.—10 to 15.

*Length*.—61.0 cm to 71.0 cm.

*Diameter*.—5.0 mm to 6.0 mm.

*Strength*.—Strong.

*Aspect*.—Upright to slightly pendent.

*Texture*.—Smooth.

*Color*.—Green (RHS 146A).

*Internode length*.—3.5 cm to 4.5 cm.

Inflorescence description:

*Appearance*.—Upright to slightly pendent, panicle inflorescence with bilaterally symmetrical flowers that open in succession beginning with the lowermost flower.

*Number of inflorescences*.—2.

*Inflorescence size*.—Height (from base to tip): 400.0 mm to 430.0 mm.

*Flowering time*.—First flowers can be expected 10 to 11 months after planting in a 12-cm pot.

*Flower*.—Height: 93.0 mm to 98.0 mm. Diameter: 105.0 mm to 110.0 mm. Depth of lip: 26.0 mm to 28.0 mm.

*Flower shape*.—Concave.

*Flower longevity*.—On the plant: 11 to 13 weeks.

*Fragrance*.—Absent.

*Flower bud*.—Average size: Large. Length: 24.0 mm to 26.0 mm. Width: 19.0 mm to 21.0 mm. Shape: Egg shaped. Color: Yellow-green (RHS N144D) with a touch of light reddish-purple (RHS N78D) toward the tip.

*Petals*.—Arrangement: Open/free. Shape: Semi-circular. Apex: Rounded asymmetric. Margin: Entire. Length (from base to tip): 63.0 mm to 65.0 mm. Width: 47.0 mm to 49.0 mm. Position of the broadest part of the petal: Toward the base. Color (when fully opened): Upper surface: Basic color: White (RHS NN155C). Over color: Absent. Lower surface: Basic color: White (RHS NN155C). Over color: Absent. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Slightly emarginated symmetric. Margin: Entire. Length (from base to tip): 52.0 mm to 54.0 mm. Width: 36.0 mm to 38.0 mm. Position of the broadest part of the dorsal sepals: At the middle. Color (when fully opened): Upper surface: Basic color: White (RHS NN155C). Over color: Absent. Lower surface: Basic color: White (RHS NN155C). Over color: Light reddish-purple (RHS N78D). Number of spots and stripes on the dorsal sepals (upper surface): None. Color of spots and stripes on the dorsal sepals (upper surface): Not applicable. Density of netting of the dorsal sepals (upper surface): None. Color of the netting (upper surface): Not applicable.

*Lateral sepals*.—Shape: Ovate. Apex: Obtuse asymmetric. Margin: Entire. Length (from base to tip): 51.0 mm to 53.0 mm. Width: 29.0 mm to 31.0 mm. Position of the broadest part of the lateral sepals: Toward the base. Color (when fully opened): Upper surface: Basic color: White (RHS NN155C). Over color: Light yellow-green (RHS 145D). Lower surface: Basic color: White (RHS NN155C). Over color: Light yellow-green (RHS 145C) and light reddish-purple (RHS N78D) on one side. Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 36.0 mm to 38.0 mm. Color of whiskers: White (RHS NN155C) with light yellow-green (RHS 2C) tips. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Moderately undulated. Length: 23.0 mm to 25.0 mm. Width: 17.0 mm to 19.0 mm. Color: Upper surface: Purplish-red (RHS 70A) and pink stripes at the base toward one margin (RHS 182C); greenish-yellow towards margin on one side (RHS 151D); white toward the other margin and the tip (RHS NN155C). Lower surface: Greenish-yellow toward margin on one side (RHS 151C); white toward the other margin and the tip (RHS NN155C). Number of spots and stripes on the lateral lobe: Few stripes. Color of spots and stripes on the lateral lobe: RHS 70A and RHS 182A. Density of netting of the lateral lobe: None. Color of the netting: None.

*Apical lobe*.—Shape: Triangular. Margin: Entire. Length: 24.0 mm to 26.0 mm. Width: 26.0 mm to 27.0 mm. Color: Upper surface: Reddish-orange margin (RHS 176C) and yellow-green at the base (RHS 154C); white (RHS NN155C) toward whiskers. Lower surface: Yellow-green at the base (RHS 154D); white (RHS NN155C) toward whiskers. Number of spots and stripes on the apical lobe: None. Color of spots and stripes on the apical lobe: Not applicable. Density of netting of the apical lobe: None. Color of the netting: Not applicable. Bump and ridge: Absent.

*Callus*.—Average size: Medium. Height: 8.0 mm to 9.0 mm. Length: 6.0 mm to 7.0 mm. Width: 4.0 mm to 5.0 mm. Color: Light greenish-yellow (RHS 3C) on sides, yellow (RHS 7B) on the upper side and toward tips and reddish-orange dots (RHS 176D).

Reproductive organs:

*Column*.—Length: 9.0 mm to 10.0 mm. Diameter: 5.0 min to 6.0 mm. Color: White at the, base (RHS NN155C).

*Pollinia*.—Quantity: 2. Diameter: 0.9 mm to 1.0 mm. Color: Orange-yellow (RHS 23A).

*Ovary*.—Length: 10.0 mm to 12.0 mm. Diameter: 2.5 mm to 2.7 mm.

*Pedicel*.—Length: 39.0 mm to 41.0 mm. Diameter: 2.8 mm to 3.1 mm. Color: Yellow-green (RHS 144B) at the base; light yellow-green (RHS 145C) with a touch of very light purple (RHS 76D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA191366' differs from the female parent plant '00001-4911' (unpatented) in that 'PHA191366' has slightly emarginated apex of dorsal sepal, rounded apex, and incurving longitudinal axis, whereas '00001-4911' has obtuse apex of dorsal sepal, emarginated apex, and recurving longitudinal axis.

'PHA191366' differs from the male parent plant 'PHALFYTBE' (U.S. Plant Pat. No. 30,484) in that 'PHA191366' has moderately compressed petals, rounded apex, and incurving longitudinal axis, whereas 'PHALFYTBE' has moderately compressed to medium petals, obtuse apex, and straight longitudinal axis.

'PHA191366' is most similar to the commercial *Phalaenopsis* plants named 'PHALHETWER' (U.S. Plant Pat. No. 33,526) and 'PHALFUBNE' (U.S. Plant Pat. No. 30,395). 'PHA191366' differs from the commercial variety 'PHALHETWER' in that 'PHA191366' has strong curvature of lateral lobe, moderately elongated leaves, and shorter internode length, whereas 'PHALHETWER' has medium curvature of lateral lobe, very elongated leaves, and longer internode length.

'PHA191366' differs from the commercial variety 'PHALFUBNE' in that 'PHA191366' has strong curvature of lateral lobe, panicle inflorescence, and long flowers in upper view, whereas 'PHALFUBNE' has medium curvature of lateral lobe, raceme inflorescence, and long to very long flowers in upper view.

I claim:

1. A new and distinct variety of *Phalaenopsis* plant named 'PHA191366', substantially as described and illustrated herein.

* * * * *